United States Patent
Stumber et al.

(10) Patent No.: US 9,492,647 B2
(45) Date of Patent: Nov. 15, 2016

(54) MICRONEEDLE ARRAY APPLICATOR AND METHOD FOR APPLYING A MICRONEEDLE ARRAY

(71) Applicant: Robert Bosch GmbH, Stuttgart (DE)

(72) Inventors: Michael Stumber, Korntal-Muenchingen (DE); Martina Daub, Weissach (DE)

(73) Assignee: Robert Bosch GmbH, Stuttgart (DE)

( * ) Notice: Subject to any disclaimer, the term of this patent is extended or adjusted under 35 U.S.C. 154(b) by 797 days.

(21) Appl. No.: 13/706,501

(22) Filed: Dec. 6, 2012

(65) Prior Publication Data

US 2013/0165902 A1 Jun. 27, 2013

(30) Foreign Application Priority Data

Dec. 23, 2011 (DE) .................. 10 2011 089 723

(51) Int. Cl.
*A61M 37/00* (2006.01)

(52) U.S. Cl.
CPC .. *A61M 37/0015* (2013.01); *A61M 2037/0023* (2013.01); *A61M 2037/0061* (2013.01)

(58) Field of Classification Search
CPC ............. A61M 37/0015; A61M 2037/0023; A61M 2037/0053; A61M 2037/0046; A61M 2037/0061
USPC .......................................... 604/173, 22, 131
See application file for complete search history.

(56) References Cited

U.S. PATENT DOCUMENTS

| | | | |
|---|---|---|---|
| 8,506,530 B2 * | 8/2013 | Laermer et al. ............. | 604/173 |
| 9,017,289 B2 * | 4/2015 | Backes ............. | A61M 37/0015 604/173 |
| 2002/0082543 A1 | 6/2002 | Park et al. | |
| 2002/0169411 A1 * | 11/2002 | Sherman ............... | A61B 5/1411 604/48 |
| 2003/0083618 A1 * | 5/2003 | Angel ............... | A61M 5/14248 604/141 |
| 2005/0165358 A1 * | 7/2005 | Yeshurun .......... | A61M 37/0015 604/173 |
| 2006/0051404 A1 * | 3/2006 | Yeshurun ............. | A61B 17/205 424/449 |
| 2008/0167601 A1 * | 7/2008 | Laermer et al. ................. | 604/22 |
| 2009/0054842 A1 * | 2/2009 | Yeshurun ............. | A61B 5/1411 604/173 |
| 2009/0187167 A1 * | 7/2009 | Sexton .................. | A61B 17/205 604/891.1 |
| 2009/0198189 A1 * | 8/2009 | Simons ............. | A61M 37/0015 604/173 |
| 2011/0212485 A1 * | 9/2011 | Mitragotri .............. | C12M 23/28 435/29 |
| 2011/0295149 A1 * | 12/2011 | Mitragotri .............. | A61B 10/02 600/566 |
| 2013/0006196 A1 * | 1/2013 | Sonderegger ......... | A61M 5/148 604/228 |

FOREIGN PATENT DOCUMENTS

| | | |
|---|---|---|
| WO | 2006055795 A1 | 5/2006 |
| WO | 2008053481 A1 | 5/2008 |

* cited by examiner

*Primary Examiner* — Gerald Landry, II
(74) *Attorney, Agent, or Firm* — Maginot, Moore & Beck LLP

(57) ABSTRACT

A microneedle array applicator is configured to apply a microneedle array in cosmetic and medical applications. The microneedle array applicator has a holding apparatus configured to define detachable holding of a microneedle array comprising a planar substrate. The microneedle array applicator also has a drive mechanism for driving the microneedle array in a first direction perpendicular to the planar substrate and in a second direction parallel to the planar substrate. A method for applying a microneedle array includes the microneedle array applicator enabling safe breaking off of the microneedles, optionally laden with an active ingredient, in the skin.

11 Claims, 2 Drawing Sheets

MICRONEEDLE ARRAY APPLICATOR AND METHOD FOR APPLYING A MICRONEEDLE ARRAY

This application claims priority under 35 U.S.C. §119 to patent application no. DE 10 2011 089 723.2, filed on Dec. 23, 2011 in Germany, the disclosure of which is incorporated herein by reference in its entirety.

BACKGROUND

The present disclosure relates to a microneedle array applicator and a corresponding method for applying microneedle arrays in cosmetic and medical applications.

Microneedle arrays are microneedles, e.g. of silicon or a biodegradable polymer, which are arranged in a grid. For specific cosmetic and/or medical applications, all needles of an array should simultaneously pierce the skin and subsequently break off in a defined fashion. In the process, a medicament or an active ingredient, optionally deposited on or in the needles, is applied into the skin.

WO 2006055795 A1 discloses a microneedle array applicator with a microneedle array in the middle of the inner side of an outwardly convex, sheet-like symmetric carrier. The microneedle array is at a distance from a contact area as a result of the convex shape of the carrier. In the case of central pressure from the outside onto the carrier, the microneedle array is moved perpendicular to the contact area toward the latter.

WO 2008053481 A1 describes a microneedle array applicator for applying microneedle arrays in cosmetic and medical applications, said microneedle array applicator having a holding apparatus for defined detachable holding of a microneedle array comprising a planar substrate. The needles of the microneedle array pierce the skin by means of a striking apparatus. A vibration mechanism is proposed for breaking off the needles.

US 20020082543 A1 discloses a microneedle array with needles with predetermined breaking points and proposes that the needles be shorn off.

SUMMARY

The present disclosure provides a microneedle array applicator according to the below description and a method for applying a microneedle array according to the below description, which allow the microneedle array to pierce safely with a subsequent reproducible, targeted breaking off of the needles.

To this end, the microneedle array applicator according to the disclosure has a drive mechanism for driving the microneedle array in a first direction perpendicular to the planar substrate and in a second direction parallel to the planar substrate.

According to the method according to the disclosure, the microneedle array is initially moved in a first direction perpendicular to the planar substrate and the microneedle array is subsequently moved in a second direction parallel to the planar substrate. Finally, microneedles of the microneedle array are shorn.

Preferred developments are the subjects of the below description.

According to the disclosure, the needles are broken off in a defined manner during an application in the skin. This supports the safe application of the needles and, optionally, of the medicament/substance laden on the needles in the skin.

BRIEF DESCRIPTION OF THE DRAWINGS

The present disclosure will be explained in more detail below on the basis of the exemplary embodiments specified in the schematic figures of the drawings.

The attached drawings should impart further understanding of the embodiments of the disclosure. They illustrate embodiments and, in conjunction with the description, serve to explain principles and concepts of the disclosure. Other embodiments and many of the aforementioned advantages emerge in view of the drawings. The elements of the drawings are not necessarily drawn to scale in respect of one another.

In the figures of the drawings, equivalent and functionally equivalent elements, features and components, or elements, features and components having the same effect, are—provided there is nothing to the contrary—respectively provided with the same reference signs.

DETAILED DESCRIPTION

Figure 1:
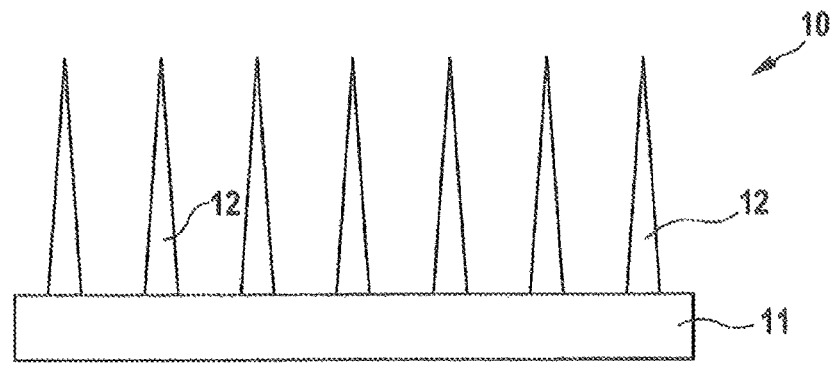
FIG. 1 shows, in a lateral view, a schematic illustration of a microneedle array for use in a microneedle array applicator as per one embodiment of the present disclosure.

FIG. 1 illustrates a microneedle array 10 for use in a microneedle array applicator. The microneedle array 10 has a planar substrate 11, out of which microneedles 12 which are arranged in regular fashion in an array stick with axes perpendicular to the substrate 11. The microneedles 12 preferably consist of silicon or a biodegradable polymer. The microneedles 12 can, internally or externally, be laden with an active ingredient in the region of the tip thereof. The microneedles 12 can have a predetermined breaking point (not illustrated), which allows the tip to be deposited in the skin. The length of the needles and, optionally, the position of the predetermined breaking point are determined from the purpose of the treatment.

Figure 2:
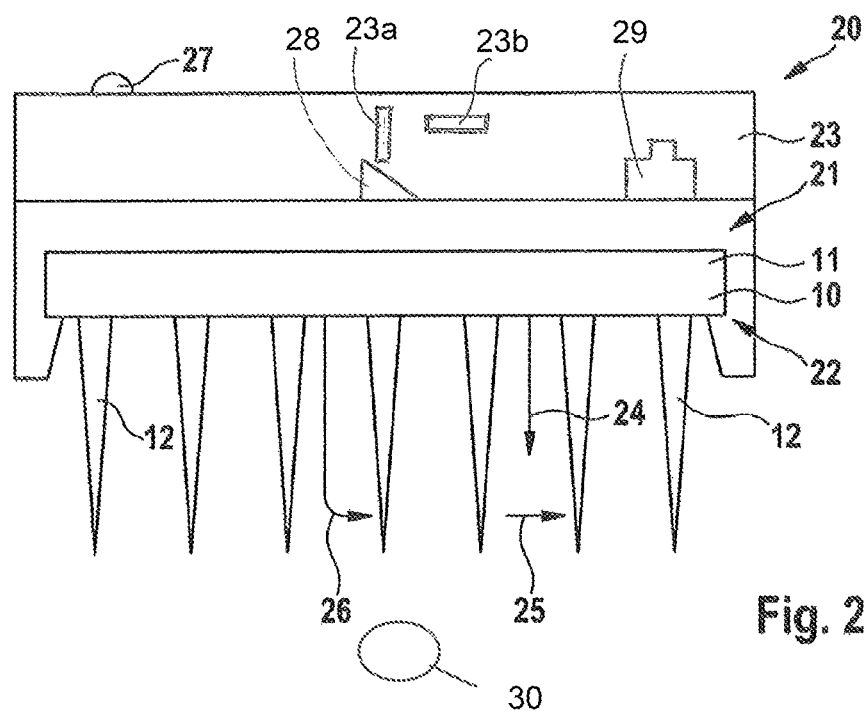
FIG. 2 shows, in a lateral view, a schematic illustration of a microneedle array applicator with a microneedle array as per the embodiment of the present disclosure.

FIG. 2 shows a microneedle array applicator 20 with the microneedle array 10 from FIG. 1. The microneedle array applicator 20 for example consists of polymeric material. The microneedle array applicator 20 has a planar holding apparatus 21 for holding the microneedle array 10, with a detachable snap connection 22 by means of latching teeth. Alternatively, the holding apparatus 21 can have an adhesive layer for detachably affixing the microneedle array 10. As a result of detachably holding the microneedle array 10, the microneedle array applicator 20 can be reused for further microneedle arrays 10.

The microneedle array applicator 20 furthermore has a drive mechanism 23 for driving the microneedle array 10 in a first direction 24 perpendicular to the planar substrate 11 and in a second direction 25 parallel to the planar substrate 11.

In one embodiment of the microneedle array applicator 20, the drive mechanism 23 has a first actuator 23a for providing drive in the first direction 24 and a second actuator 23b for providing drive in the second direction 25.

In an alternative embodiment of the microneedle array applicator 20, the drive mechanism 23 has a deflection apparatus 28 for deflecting the movement of the microneedle array from the first direction 24 into the second direction 25 such that, during operation, there is a movement of the microneedle array along the arrow 26.

According to a further embodiment of the microneedle array applicator 20, the drive mechanism 23 has a striking apparatus 29 for driving the microneedle array 10. In particular, the striking apparatus 29 can strike an edge of the holding apparatus 21 or an edge of the microneedle array 10 and thereby promote the microneedles 12 breaking off.

According to a further embodiment of the microneedle array applicator 20, the drive mechanism 23 may be configured to carry out a rotational movement 30 of the microneedle array 10.

The drive mechanism 23 is triggered by actuating a trigger 27.

Figure 3:
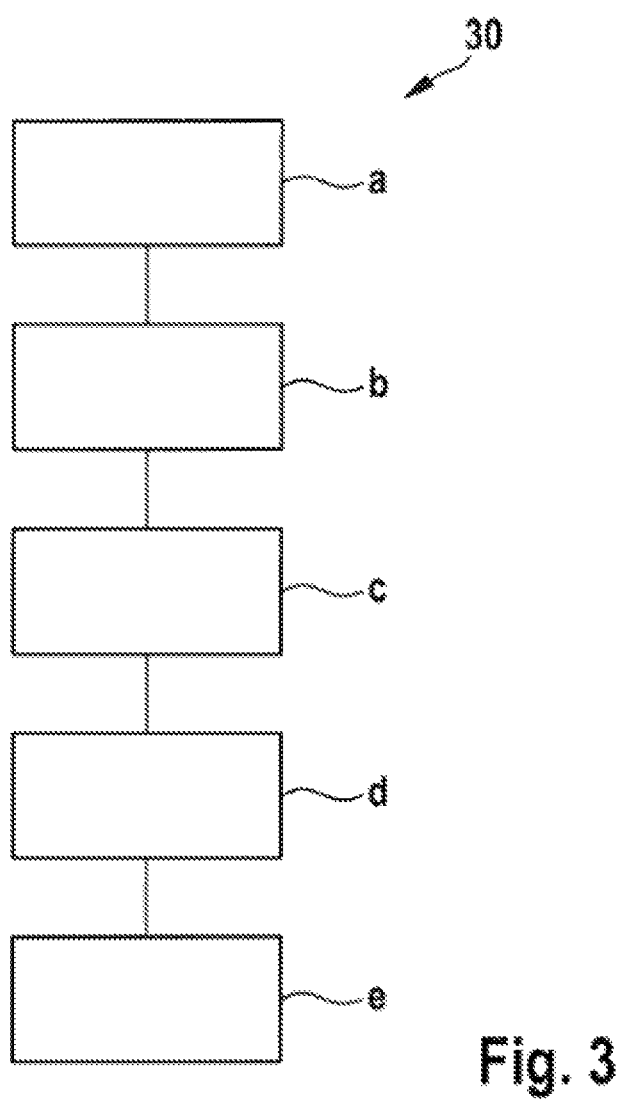
FIG. 3 shows a flowchart of the method for applying a microneedle array as per a further embodiment of the present disclosure.

FIG. 3 shows a flowchart 30 of the method according to the disclosure for applying a microneedle array comprising a planar substrate. For clarification purposes, the method is described with reference to the microneedle array applicator 20 in FIG. 2. The method starts with method step a): positioning the microneedle array 10 in a microneedle array applicator 20. To this end, the microneedle array is affixed in a holding apparatus by means of an adhesive layer or a snap connection 22.

Now, the microneedle array applicator 20 is placed onto a point on the skin to be treated in method step b).

In method step c), which is initiated by actuating the trigger 27, the microneedle array 10 is moved in a first direction 24 perpendicular to the planar substrate 11. The needles of the microneedle array 10 now penetrate the point on the skin.

This is subsequently automatically followed by method step d), moving the microneedle array 10 in a second direction 25 parallel to the planar substrate 11. During the movement parallel to the planar substrate 11 in the second direction 25, the microneedles 12 of the microneedle array 10 are shorn in method step e). In the process, the skin resists the lateral movement of the needles, which resistance promotes the shearing.

The microneedle array applicator 20 is now removed from the point on the skin. The needle tips remain in the skin. As a result, both the needle tips and, optionally, active ingredients with which the needle tips are laden are reliably applied into the skin.

The movement of the microneedle array 10 can be brought about in a variety of ways; the following preferred embodiments of the method relate to method steps c) and d). In one embodiment of the method, the movement of the microneedle array 10 in the first direction 24 and in the second direction 25 is respectively brought about with an associated mechanism.

In an alternative embodiment of the method, the movement of the microneedle array 10 is brought about with a single drive mechanism 23 and a deflection apparatus for deflecting a movement of the microneedle array 10 from the first direction 24 into the second direction 25.

The movement of the microneedle array in the second direction is preferably brought about in highly dynamic fashion.

According to a further embodiment of the method, the microneedle array 10 is moved in at least one direction by means of a striking apparatus for driving the microneedle array 10. The striking apparatus enables a highly dynamic movement, particularly in the second direction 25, both in the case of a separate drive in the second direction 25 and in the case of a drive in the first direction 24 with a deflection from the first direction 24 into the second direction 25 as per the arrow 26.

According to a further embodiment of the method, the movement of the microneedle array 10 comprises a rotational movement of the microneedle array 10.

The path in the orthogonal direction is preferably kept as short as possible in order to avoid unnecessary injury in the skin. Automatic actuation should be preferred in all cases to manual piercing for reasons of reproducibility and ease of application.

Although the present disclosure was described completely above on the basis of preferred exemplary embodiments, it is not restricted thereto but rather can be modified in various ways.

What is claimed is:

1. A microneedle array applicator for applying a microneedle array in cosmetic and medical applications comprising:
   a holding apparatus for defined detachable holding of a microneedle array comprising a planar substrate; and
   a drive mechanism configured to drive the microneedle array in a first direction perpendicular to the planar substrate and in a second direction parallel to the planar substrate, wherein the drive mechanism has a deflection apparatus configured to deflect a movement of the microneedle array from the first direction into the second direction.

2. The microneedle array applicator according to claim 1, wherein the drive mechanism has a first actuator configured to provide drive in the first direction and a second actuator configured to provide drive in the second direction.

3. The microneedle array applicator according to claim 1, wherein the drive mechanism has a striking apparatus configured to drive the microneedle array.

4. The microneedle array applicator according to claim 1, wherein the drive mechanism is configured to carry out a rotational movement of the microneedle array.

5. The microneedle array applicator according to claim 1, wherein the holding apparatus has an adhesive layer or a snap connection.

6. A method for applying a microneedle array having a planar substrate, comprising:
   positioning the microneedle array in a microneedle array applicator;
   placing the microneedle array applicator onto a point on the skin;
   moving the microneedle array in a first direction perpendicular to the planar substrate;
   moving the microneedle array in a second direction parallel to the planar substrate, wherein the microneedle array is moved by a drive mechanism and a deflection apparatus configured to deflect a movement of the microneedle array from the first direction into the second direction; and
   shearing microneedles of the microneedle array.

7. The method according to claim 6, wherein the microneedle array is moved in the first direction and in the second direction by an associated actuator.

8. The method according to claim 6, wherein the microneedle array is moved in the second direction in highly dynamic fashion.

9. The method according to claim 6, wherein the microneedle array is moved by a striking apparatus configured to drive the microneedle array.

10. The method according to claim 6, wherein the movement of the microneedle array comprises a rotational movement of the microneedle array.

11. The method according to claim 6, wherein the microneedle array is affixed in a holding apparatus by an adhesive layer or a snap connection.

\* \* \* \* \*